United States Patent
Berkshire et al.

(10) Patent No.: US 11,972,846 B1
(45) Date of Patent: Apr. 30, 2024

(54) HEALTHCARE WORKER SMART VISOR

(71) Applicant: T-Mobile Innovations LLC, Overland Park, KS (US)

(72) Inventors: Matthew Berkshire, Roselle, IL (US); Zhisheng Chen, Overland Park, KS (US); Griffin Cruz Garbutt, Austin, TX (US); Joao Teixeira, Shawnee, KS (US); Shant Thomas, Lawrence, KS (US)

(73) Assignee: T-Mobile Innovations LLC, Overland Park, KS (US)

( * ) Notice: Subject to any disclaimer, the term of this patent is extended or adjusted under 35 U.S.C. 154(b) by 469 days.

(21) Appl. No.: 17/210,329

(22) Filed: Mar. 23, 2021

(51) Int. Cl.
| | |
|---|---|
| *G06Q 50/00* | (2012.01) |
| *G06T 3/40* | (2006.01) |
| *G06V 40/12* | (2022.01) |
| *G06V 40/16* | (2022.01) |
| *G10L 15/22* | (2006.01) |
| *G16H 10/60* | (2018.01) |
| *G16H 20/10* | (2018.01) |
| *G16H 40/63* | (2018.01) |
| *H04B 1/3827* | (2015.01) |

(52) U.S. Cl.
CPC .............. *G16H 10/60* (2018.01); *G06T 3/40* (2013.01); *G06V 40/1365* (2022.01); *G06V 40/172* (2022.01); *G10L 15/22* (2013.01); *G16H 20/10* (2018.01); *G16H 40/63* (2018.01); *H04B 1/385* (2013.01); *G10L 2015/223* (2013.01); *H04B 2001/3866* (2013.01)

(58) Field of Classification Search
CPC ........ G16H 10/60; G16H 20/10; G16H 40/63; G06V 40/1365; G06V 40/172; G06T 3/40; G10L 15/22; H04B 1/385
See application file for complete search history.

(56) References Cited

U.S. PATENT DOCUMENTS

| | | | |
|---|---|---|---|
| 2006/0139136 A1* | 6/2006 | Hornegger | A61B 6/4441 335/299 |
| 2012/0166203 A1* | 6/2012 | Fuchs | G16H 40/20 704/E11.001 |

FOREIGN PATENT DOCUMENTS

| | | | | |
|---|---|---|---|---|
| WO | WO-2018140415 A1 * | 8/2018 | ......... | A61B 1/00011 |
| WO | WO-2022125845 A1 * | 6/2022 | | |

* cited by examiner

*Primary Examiner* — Rajesh Khattar

(57) ABSTRACT

A healthcare worker smart visor. The smart visor comprises a radio transceiver, a non-transitory memory, a camera, a processor communicatively coupled to the radio transceiver, the non-transitory memory, and the camera, an optical visor, a head-up display projector that is communicatively coupled to the processor and that is operable to project an image on an inside surface of the optical visor, a headband retaining the radio transceiver, the non-transitory memory, the camera, the processor, the optical visor, and the head-up display projector, and a smart visor application stored in the non-transitory memory that, when executed by the processor performs two-factor authentication of a healthcare worker, transmits a request for current indications of healthcare equipment via the radio transceiver to the healthcare equipment based on the identity of the healthcare equipment, and presents the current indications on the inside surface of the optical visor via the head-up display.

13 Claims, 8 Drawing Sheets

HEALTHCARE WORKER SMART VISOR

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Advances in technology have been applied to healthcare in various ways. Sophisticated diagnostics tools have been developed based on new technology. Healthcare professionals are trained to use these new tools in the performance of their tasks. As technology advances, new opportunities for improving healthcare delivery emerge.

SUMMARY

In an embodiment, a healthcare worker smart visor is disclosed. The healthcare worker smart visor comprises a radio transceiver, a non-transitory memory, a camera, a processor communicatively coupled to the radio transceiver, the non-transitory memory, and the camera, an optical visor, a head-up display projector that is communicatively coupled to the processor and that is operable to project an image on an inside surface of the optical visor, a headband retaining the radio transceiver, the non-transitory memory, the camera, the processor, the optical visor, and the head-up display projector, and a smart visor application stored in the non-transitory memory. When executed by the processor, the smart visor application transmits a digital image captured by the camera via the radio transceiver to a facial recognition server application that executes on a computer system, receives an identity of a patient via the radio transceiver in response to transmitting the digital image captured by the camera, transmits a request for patient information via the radio transceiver to a patient information server application executing on a computer system, wherein the request comprises the identity of the patient associated with the digital image, receives patient information via the radio transceiver in response to transmitting the request for patient information, and presents at least some of the patient information on the inside surface of the optical visor via the head-up display projector. The smart visor application also receives patient body metrics via the radio transceiver from sensors associated with the patient and presents at least some of the body metrics on the inside surface of the optical visor, whereby a healthcare worker positively identifies the patient and provides healthcare to the patient according to an authorized treatment regime.

In another embodiment, a method of supporting a healthcare worker treat a patient is disclosed. The method comprises recording an audio of a healthcare worker by a smart visor application executing on a processor of a healthcare worker smart visor, transmitting a request comprising the audio recording to perform voice recognition by the smart visor application via a radio transceiver of the healthcare worker smart visor, capturing a fingerprint biometric by the smart visor application, transmitting a request comprising the fingerprint biometric to perform fingerprint recognition by the smart visor application via the radio transceiver, and completing a two-factor authentication of the healthcare worker by the smart visor application based on the transmitted audio recording and the transmitted fingerprint biometric. The method further comprises, based on successful completion of two-factor authentication, requesting patient information by the smart visor application via the radio transceiver, receiving patient information by the smart visor application via the radio transceiver, and presenting at least some of the patient information by the smart visor application on an inside surface of an optical visor of the healthcare worker smart visor. The method further comprises capturing a digital image of healthcare equipment by the smart visor application, based on the digital image of healthcare equipment, identifying the healthcare equipment by the smart visor application, transmitting a request for current indications by the smart visor application via the radio transceiver to the healthcare equipment, receiving current indications of the healthcare equipment by the smart visor application via the radio transceiver, and presenting the current indications of the healthcare equipment on the inside surface of the optical visor of the healthcare worker smart visor, whereby a healthcare worker is supported in treating a patient.

In yet another embodiment, a healthcare worker smart visor is disclosed. The healthcare worker smart visor comprises a radio transceiver, a non-transitory memory, a camera, a processor communicatively coupled to the radio transceiver, the non-transitory memory, and the camera, an optical visor, a head-up display projector that is communicatively coupled to the processor and that is operable to project an image on an inside surface of the optical visor, a headband retaining the radio transceiver, the non-transitory memory, the camera, the processor, the optical visor, and the head-up display projector, and a smart visor application stored in the non-transitory memory. When executed by the processor, the smart visor application performs two-factor authentication of a healthcare worker, transmits a digital image captured by the camera via the radio transceiver to a healthcare equipment recognition server application that executes on a computer system, receives an identity of the healthcare equipment via the radio transceiver in response to transmitting the digital image captured by the camera, transmits a request for current indications via the radio transceiver to the healthcare equipment based on the identity of the healthcare equipment, presents the current indications on the inside surface of the optical visor via the head-up display projector. The smart visor application further receives patient information via the radio transceiver in response to transmitting a request for patient information, presents at least some of the patient information on the inside surface of the optical visor via the head-up display projector, receives a voice prompt from a healthcare worker wearing the healthcare worker smart visor requesting information on interactions with a specific drug, and presents information about interactions with the specific drug on the inside surface of the optical visor via the head-up display projector.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief descrip

DETAILED DESCRIPTION

Figure 1A:
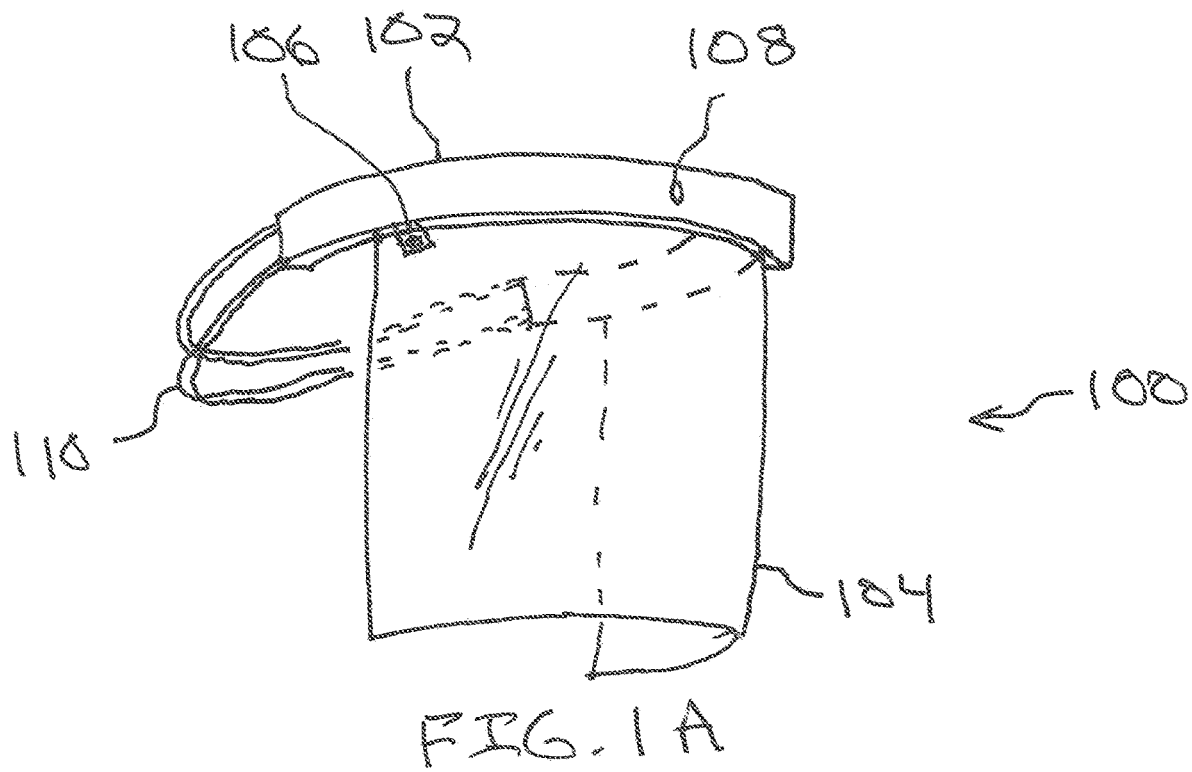
- FIG. 1A and FIG. 1B are illustrations of a healthcare worker smart visor according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The present disclosure teaches a healthcare worker smart visor that attenuates transmission of pathogens while at the same time providing the healthcare worker with useful communication services and augmented reality functions that assist the worker in performing his or her work. The smart visor comprises an optical visor which allows the healthcare worker to see a patient and equipment while attenuating transmission of pathogens from the worker to the patient and from the patient to the worker. The smart visor comprises a headband that retains the optical visor in front of the worker's face and also houses a variety of electronic equipment. A head-up-display projector retained by the headband can project images on an inside surface of the optical visor which are focused at infinity or mid-range, allowing the worker to read information projected onto the interior surface of the optical visor while his or her eyes remain focused beyond the optical visor on a patient or on healthcare equipment.

The smart visor may have an interface that allows the worker to control the display presented by the HUD projector. For example, the worker may provide voice commands, and an interactive voice recognition (IVR) driver executing on a processor retained by the headband may translate the voice commands to digital messages suitable to control the HUD projector and other applications executing on the processor. The worker may command the HUD projector to present current values of the patient vital signs in the center of the optical visor. Alternatively, the worker may command the HUD projector to present the values of vital signs in a left quadrant of the optical visor or to remove the presentation of vital signs entirely. Likewise the worker may be able to control other functions of the healthcare worker smart visor by speaking other verbal commands that are translated by the IVR driver to digital messages suitable to applications providing these other functions. Particular challenges for providing augmented reality (AR) features such as this in the healthcare context may involve modes and flexibility of presentation to get information in the field-of-view where needed but still provide clearance for adequate views of the patient to get healthcare work done. The healthcare smart visor provides a particular technical solution to this technical problem.

In an embodiment, the healthcare worker smart visor may be pre-programmed to display data or images on the inside surface of the optical visor so as to avoid interference with the healthcare worker engaging with the reality beyond the optical visor—engaging with the patient, with medical equipment, with medicines. The smart visor may interwork with a server application to assist the healthcare worker complete a care routine or procedure. The smart visor can identify which portion of the care routine it is in based on following the pattern of verbal instruction or based on processing of images taken with a digital camera of the headband to associate certain images with certain steps in the care routine. If medication is being identified and presented—the smart visor can recognize a dispensing container or measurement tool and specifically avoid projecting data in the way of that container or tool as seen through the optical visor. Similarly, if it is time to treat a certain area of the patient—the smart visor can avoid presenting information over that area (moving the information depending on where the camera suggests that area is) or targeting specific information integrating with that area (proposed injection site mapped on arm or other physical injection location) while reducing noise in that area (no vital signs, but yes targeting diagram). Even in the absence of a sequenced care routine, just based on what it sees is being picked up and scanned and done—it can avoid projecting over key sources of information for the healthcare worker (the face, a site being worked on, a readout, monitor, container, or tool).

As used herein augmented reality (AR) refers to the healthcare worker smart visor blending data and images processed electronically and presented via the head-up display projector on the inside surface of the optical visor with the live image seen through the optical visor of the patient, medical equipment, and treatment room. The 'reality' portion of this term may be said to refer to what is seen beyond the transparency of the optical visor, while the 'augmented' portion of this term may be said to refer to what is seen on or reflected off the inside surface of the optical visor (e.g., data, procedures instructions, values of sensor readings, etc.). Thus, the healthcare worker is seeing 'reality' PLUS complimentary, helpful information.

In an embodiment, the healthcare worker smart visor headband retains a radio transceiver which provides reliable and secure communication access to the communication network. In an embodiment, the radio transceiver is a cellular radio transceiver and establishes a wireless communication link to a cell site which communicatively couples the healthcare smart visor to a network. In an embodiment, the radio transceiver is a WiFi or a BlueTooth radio transceiver and establishes a wireless communication link to an access point (AP) which communicatively couples the healthcare smart visor to a network. In an embodiment, the healthcare smart visor comprises a plurality of radio transceivers.

The healthcare worker smart visor headband may retain a digital camera. The camera may capture a digital image of a patient, and the radio transceiver may send the digital image to a facial recognition server application executing on a computer system in a secure hospital private network requesting positive identification of the patient. The facial recognition server application may analyze the digital image to match to a previously captured facial signature of the patient, determine the identity of the patient, and return the patient identity in a message to the smart visor. The HUD projector may present the name of the patient on the inside surface of the optical visor. The various applications executing on the processor of the smart visor may be informed of the patient identity and retain that identity as an execution context or as a parameter value. These applications may execute based on this stored patient identity or cross-check their activities based on this stored patient identity. A problem that is sometimes experienced in healthcare environments is misidentification of patients, resulting in providing the wrong treatment procedures or the wrong drug therapies to patients. The patient facial recognition functionality described herein can reduce the risk of providing wrong treatment or wrong drug therapies due to patient misidentification. The healthcare visor provides a particular technical solution to this technical problem of misidentifying patients.

In an embodiment, the healthcare worker smart visor is further able to complete a two-factor authentication of the healthcare worker, for example obtaining a biometric signature from the worker (e.g., a fingerprint scan) and a voice scan from the worker, sending these two factors to a server two-factor authentication application, and receiving the result of the two-factor authentication performed by the server. The authentication of the healthcare worker and the patient can be linked by the smart visor with accessing patient data, accessing a patient specific care plan (treatment/medication), linked with accessing a database to identify and/or confirm objects in the treatment room (e.g., medical equipment, medicine, etc.), linked with accessing inventory records matching tags on items or medication. The authentication of the healthcare worker and the patient can be linked by the smart visor to guiding and auditing the work of the healthcare worker and what they are seeing with the patient. In an embodiment, the smart visor may also provide a quick 911 link where if they call an emergency an attending can be connected to the video stream to see what is happening and immediately provide diagnosis and guidance until more support can arrive.

In an embodiment, the smart visor is able to wirelessly communicate with or scan sensors and/or recording devices that are topical, implanted, or embedded in a patient, either using cellular communication protocols or other wireless communication protocols. These sensors and/or recording devices may sense and/or record patient vital signs, for example heart rate, O2 saturation level, body temperature, blood sugar level, blood thickness, blood pressure, or other vital sign. Some of these sensors and/or recording devices may capture an electrocardiogram of the patient. The smart visor may capture data from the sensors and/or recording devices and relay them via a secure communication channel, for example via a cellular wireless link, to a patient data store in a healthcare facility private network.

In an embodiment, the use of a cellular wireless link for transmitting and/or receiving sensitive medical and/or patient confidential information may promote compliance with HIPPA (health insurance portability and accountability act) regulations and personally identifiable information (PII) handling regulations, because cellular communication links are considered secure and impervious to cyber criminals due to robust encryption techniques being used. Additionally, in an embodiment, the network slicing features of 5G communication networks may be leveraged to assure stringent quality of service demands as well as security requirements placed upon the information the smart visor will be working with. The smart visor is able to access servers in a healthcare facility private network to obtain and present information on a patient, for example a therapy or treatment plan for the patient and a list of drugs and dosages taken by the patient. The smart visor is able to access servers in a healthcare facility private network which can check a known drug regime of a patient for adverse interactions with a different drug proposed to address a current health problem of a patient. In an embodiment, edge processing may be employed between the smart visor and a communication network to reduce the loads placed on a core network by the smart visor and the systems it accesses. This may be especially desirable in a hospital where there may be many healthcare worker smart visors actively using the communication network to store data and look up information.

In an embodiment, the healthcare worker smart visor is able to provide some virtual reality (VR) functions that assist the worker in providing healthcare. For example, the smart visor may present a magnified image of a selected area of a patient's body for closer inspection—either presented so as to fill the optical visor and prevent the observing of the environment beyond the optical visor or presented in a portion of the optical visor while still allowing observing the environment beyond the optical visor in at least a portion of the optical visor. For example, the smart visor may present a simulated view of a functioning of an internal organ or other anatomical feature of a patient for assistance to the healthcare worker in visualizing a problem, visualizing where to make an incision, and where to insert a needle.

Figure 1B:
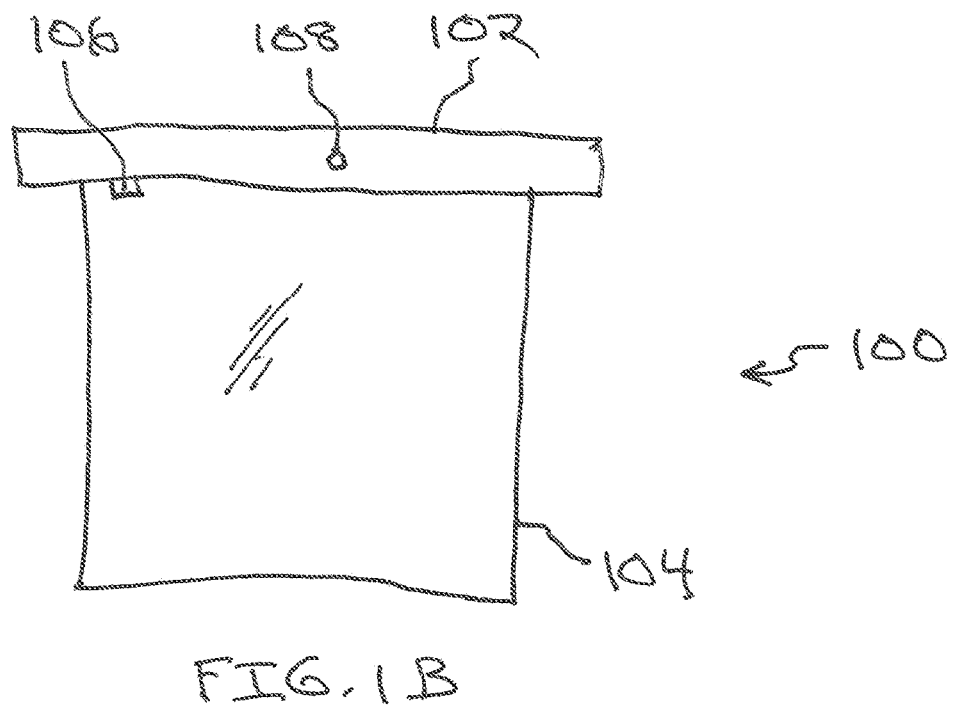

Turning now to FIG. 1A and FIG. 1B, a healthcare worker smart visor 100 is described. In an embodiment, the smart visor 100 comprises a headband 102, an optical visor 104, a head-up display (HUD) projector 106, a digital camera 108, and a retaining strap 110. The headband 102 retains the optical visor 104, the HUD projector 106, the camera 108, and other electronic devices described with reference to FIG. 2A and FIG. 2B hereinafter. The optical visor 104 provides a barrier that attenuates the transmission of pathogens from a healthcare worker wearing the smart visor 100 to a patient and from a patient to the healthcare worker. The optical visor 104 may attenuate the transmission of infectious diseases.

The optical visor 104 is transparent, allowing the healthcare worker to readily see the patient and healthcare equipment while looking through the optical visor 104. The optical visor 104, additionally, has an inside surface (e.g., a surface facing a face of the healthcare worker wearing the smart visor 100) that is suitable for projecting visual images onto. While a particular shape of an optical visor 104 is shown in FIG. 1A and FIG. 1B, it is understood that the optical visor 104 may take different shapes, for example the corners at the lower edge of the optical visor 104 depicted as about right angles could be rounded off.

The HUD projector 106 is operable to project images onto the inside surface of the optical visor 104, presenting an image visible to the healthcare worker wearing the smart visor 100 while at the same time his or her eyes are focused on a patient and/or medical equipment beyond the optical visor 104. This may be referred to as an infinity focused image or as a mid-range focused image in some contexts. In an embodiment, the optical visor 104 is a durable transparent plastic. In an embodiment, the optical visor 104 is attached to the headband 102 with a snap fit, with clips, with plastic rivets and is removable for easy replacement.

In an embodiment, the HUD projector 106 is configured to project a standard image onto the inside surface of the optical visor 104, receive a reflection from the optical visor 104, compare the reflection to the pre-defined standard image to determine a distortion of the standard image, analyze the distortion of the standard image (e.g., distortion due to imperfection and/or a curved shape of the interior surface of the optical visor 104), and adapt the projection of the standard image based on the analysis of the distortion. For example, a second digital camera (not shown) may be retained by the headband 102 inside the optical visor 104 in a position to capture the image projected by the HUD projector 106 onto the inside surface of the optical visor 104 and provide a digital image to the HUD projector 106 for analysis. In this way the HUD projector 104 is able to present a clear and accurate image to a healthcare worker wearing the smart visor 100.

The camera 108 may be installed in the headband 102 about in the middle, such that the camera is naturally directed directly ahead of the healthcare worker wearing the smart visor 100. In an embodiment, the smart visor 100 may comprise a second camera, a third camera, and possibly additional cameras located to be directed in other directions than straight forwards. For example, some of the additional cameras may be directed to capture digital images of a standard image projected onto the inside surface of the optical visor 104 and provided to the HUD projector 106 for analysis in adapting the images the HUD projector 106 projects. The retaining strap 110 serves to hold the headband 102 in place on a healthcare worker's head by elastic tension. In an embodiment, a cloth cap or cloth straps may attach above the headband 102 whereby the cap or straps hold the headband 102 and prevents it from sliding down the sides of the workers head. The retaining strap 110, cloth cap, and/or cloth straps may be detachable from the headband 102 to permit washing the retaining strap 110, cloth cap, and/or cloth straps.

It is contemplated that the healthcare worker smart visor 100 may be useful for nurses, doctors, and other workers providing healthcare services to human patients. The smart visor 100 may provide advantages and benefits in yet other work environments, such as in veterinary practices, in industrial food processing environments, in semiconductor fabrication environments, and other work environments.

Figure 2A:
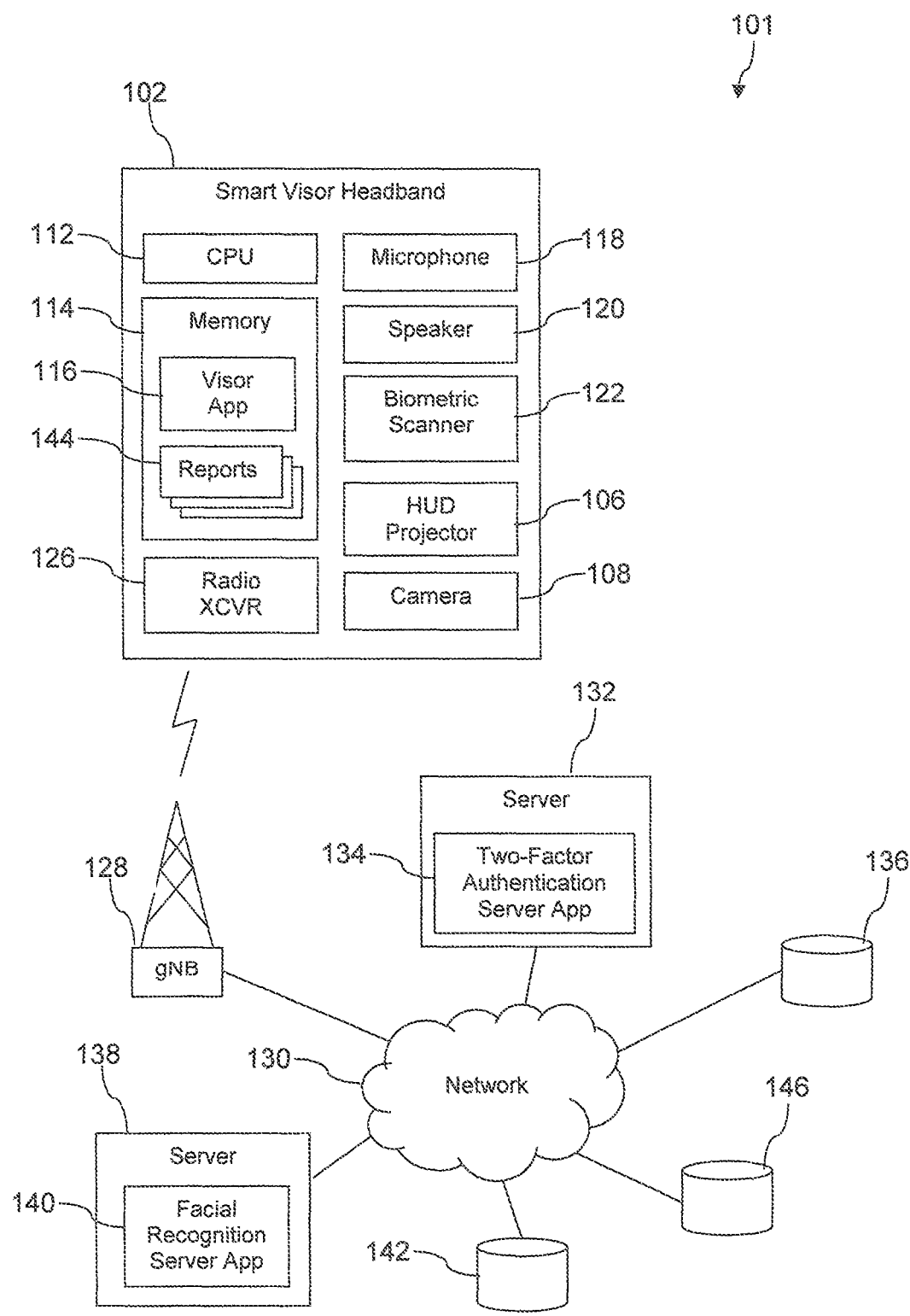
FIG. 2A and FIG. 2B are block diagrams of a communication system including a healthcare worker smart visor according to an embodiment of the disclosure.
Figure 2B:
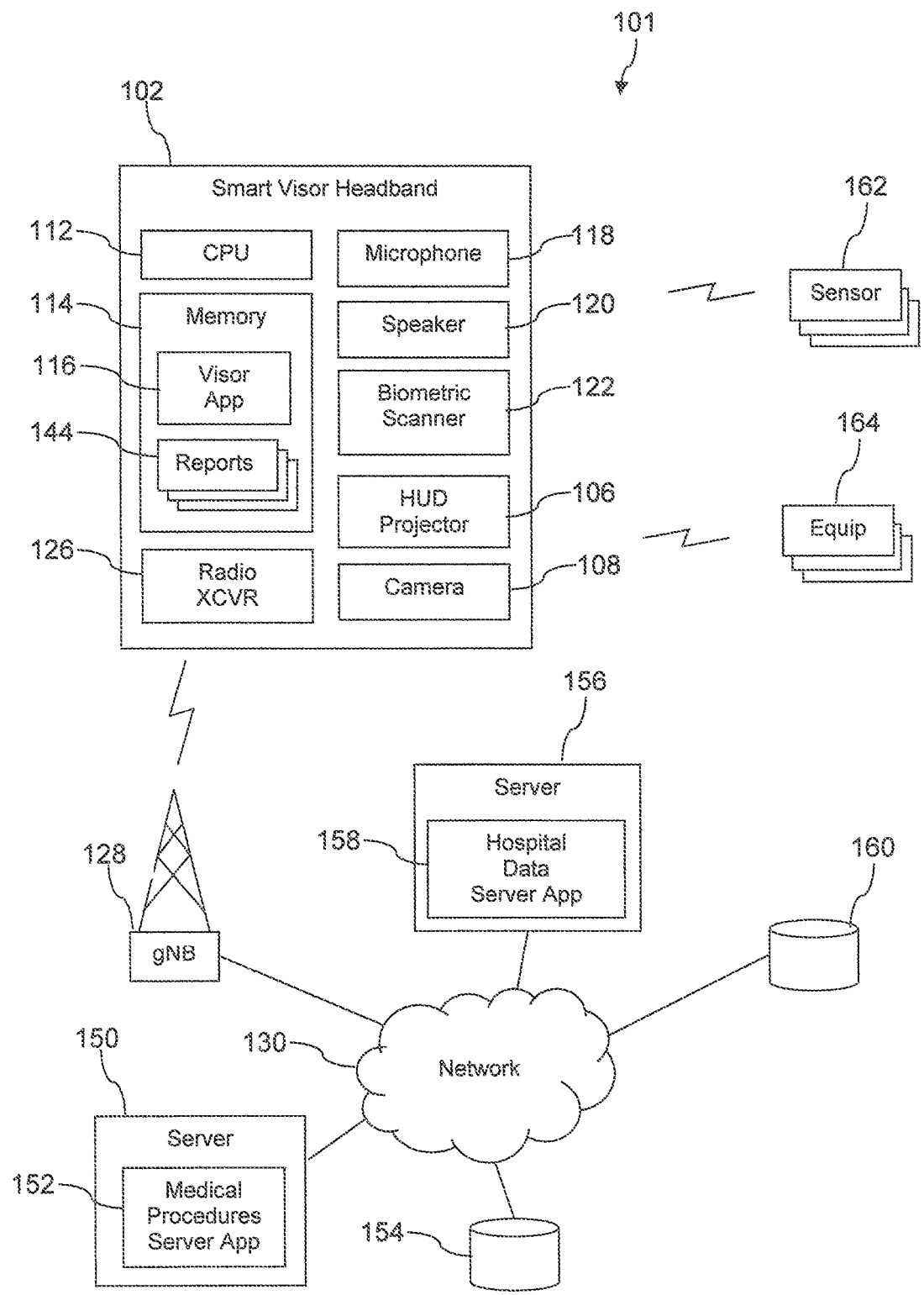

Turning now to FIG. 2A and FIG. 2B, a communication system 101 is described. In an embodiment, the headband 102 comprises a processor 112, and a memory 114 that stores a smart visor application 116 in a non-transitory memory portion of the memory 114. The headband 102 also comprises a microphone 118, a speaker 120, a biometric scanner 122, and a radio transceiver 126. Additionally, the headband 102 comprises the HUD projector 106 and the camera 108 described above with reference to FIG. 1A and FIG. 1B. The headband 102 retains a power source (not shown) such as an electric battery. In an embodiment, the power source is a rechargeable electric battery. The power source provides electric power to the HUD projector 106, the camera 108, the processor 112, the memory 114, the microphone 118, the speaker 120, and the radio transceiver 126.

In an embodiment, the radio transceiver 126 is a cellular radio transceiver and may receive a wireless communication link from a cell site 128 according to a 5G, a long-term evolution (LTE), a code division multiple access (CDMA), or a global system for mobile communications (GSM) telecommunication protocol. The cell site 128 communicatively couples the radio transceiver 126 to a network 130. The network 130 comprises one or more public networks, or a combination thereof. It is understood that most United States late generation cellular communication links are considered secure and impervious to cyber criminals due to robust encryption techniques being used. In an embodiment, the headband 102 may comprise additional radio transceivers and/or receivers not shown in FIG. 2A, and FIG. 2B, for example a WiFi radio transceiver and or a short-range radio transceiver such as a BlueTooth radio transceiver.

The visor application 116 is described as providing the logic and instructions executed by the processor 112 for all baseband processing in the headband 102. In some embodiments, however, a plurality of applications may collectively provide the functionality attributed herein to the single smart visor application 116. For example, a plurality of device drivers may be stored in the memory 114 and may be executed by the processor 112 to interface between the visor application 116 or other applications and devices such as the HUD projector 106, the camera 108, the microphone 118, the speaker 120, the radio transceiver 126 and optionally other peripheral devices of the headband 102. In an embodiment, an operating system (OS) is stored in a non-transitory portion of the memory 114 and is executed by the processor 112. The smart visor application 116 and possibly other applications may be executed in a context provided by such an OS.

In an embodiment, the smart visor application 116 engages in a two-factor authentication process to assure that the person using the smart visor 100 is authorized to access confidential and private information. In an embodiment, many of the functions of the smart visor 100 are inhibited by the smart visor application 116 until the two-factor authentication process has been completed successfully. For example, in an embodiment, the smart visor application 116 does not transmit via the cellular radio transceiver 126 or via a WiFi or a BlueTooth radio transceiver, does not receive via the radio transceiver, and does not present on the via the head-up display projector 106 until after successfully performing the two-factor authentication.

The user may be prompted via a verbal request sounded through the speaker 120 to recite a specific phrase or to read a text projected on the inside surface of the optical visor 104 by the HUD projector 106. The microphone 118 may capture this audio and relay the audio to the smart visor application 116. The user may also be prompted via a verbal request sounded through the speaker 120 to provide a fingerprint biometric by touching a fingertip or thumb-tip to the biometric scanner 122 retained by the headband 102, and the biometric scanner 122 may relay the biometric indication to the smart visor application 116. The smart visor application 116 sends the audio and the biometric indication in one message or two messages requesting two-factor authentication to a two-factor authentication server application 134 executing on a computer 132. In an embodiment, the computer 132 is located in a private domain of a healthcare facility behind a firewall of a private network maintained by the healthcare facility. Computer systems are described further hereinafter. In an embodiment the message further comprises a claimed identity of the wearer of the smart visor 100, for example Doctor Faustus. The two-factor authentication server application 134 processes the audio and fingerprint biometric indication and compares these to a voice signature and a biometric indication (e.g., a digital representation of a finger print biometric) previously stored in an authentication data store 136. If a sufficiently faithful match is confirmed by the two-factor authentication server application 134, the two-factor authentication server application 134 transmits an authentication success message, otherwise the two-factor authentication server application 134 transmits an authentication failure message.

In an embodiment, other authentication tokens may be used in the two-factor authentication process, for example a personal identification number (PIN) may be provided as one of the authentication tokens. The PIN may be input by the wearer of the smart visor 100 by selecting by verbal commands from numbers presented by the HUD projector 106 on the inside surface of the optical visor 104. These numbers may be presented in a random order whereby to thwart any attempt to eavesdrop on and learn the PIN by another. Thus, the sequence of numbers 3, 9, 7, 1, 4, 2, 6, 8, 0, 5 may be presented and displayed for about two seconds each. If the subject PIN is '1234,' the wearer may speak "third" when the 3 is presented (e.g., third number in the PIN), be silent when 9 and then 7 are presented, speak "first" when the 1 is presented, speak "fourth" when the 4 is presented, speak "second" when the 2 is presented, and be silent as 6, 8, 0, and 5 are presented. Since the sequence 3, 9, 7, 1, 4, 2, 6, 8, 0, 5 was randomly determined by the smart visor application 116 and is different each time the authentication process is performed, and because others cannot see what is reflected from the inside surface of the optical visor 104 to the eyes of the wearer, others cannot readily eavesdrop and learn the wearer's PIN. It is understood that other numbers of PIN digits may be employed.

In an embodiment, the smart visor application 116 performs a facial recognition process on a patient. For example, the camera 108 captures a digital image of the patient and provides the digital image to the smart visor application 116. The smart visor application 116 transmits the digital image via the radio transceiver 126 via the cell site 128, via the network 130, to a facial recognition server application 140 executing on a computer 138. Alternatively, the radio transceiver 126 may transmit the digital image via an access point (not shown) to the facial recognition server application 140. In an embodiment, the computer 138 is located in a private domain of a healthcare facility behind a firewall of a private network maintained by the healthcare facility. The facial recognition server application 140 searches a data store 142 comprising digital images associated with patient identities. When the digital image provided by the smart visor application 116 is deemed by the facial recognition server application 140 to match the digital image of an entry in the data store, the facial recognition server application 140 returns the identity of the patient associated with this entry to the smart visor application 116.

The smart visor application 116 may present the patient identity via the HUD projector 106 on the inside surface of the optical visor 104, for example for the wearer to match to a healthcare facility identity bracelet worn by the patient. This may provide redundant validation of the patient's identity. If any mismatches occur, the healthcare worker can pause and take actions to resolve the identity mismatch. Such a facial recognition identification can contribute to reducing the number of errors in delivering a treatment planned for patient A instead to patient B. Additionally, the patient identity returned by the facial recognition server application 140 may be used automatically by the smart visor application 116 to retrieve other patient information in the data store 142, such as contact information for a spouse or a relative of the patient, a treatment plan for the patient, a treatment history of the patient, a medical history of the patient, a list of drugs taken by the patient, a vital signs history of the patient, and the like. This information may be presented by the HUD projector 106 on the inside surface of the optical visor 104. In an embodiment, this information is retrieved and stored by the smart visor application 116 and stored in the memory 114 but not presented until the wearer of the smart visor 100 requests this presentation.

When a patient is received into the healthcare facility a digital image of the patient's face is captured and entered into the data store 142 along with an identity of the patient. Other information associated with the patient may also be stored in this data store 142 associated with the identity of the patient. Alternatively, other information about the patient may be stored in a separate data store associated with the identity of the patient, such that by providing the patient identity this other information can be accessed.

In an embodiment, the smart visor application 116 supports creation of reports. Healthcare workers may generate reports on their activities including capturing vital signs, identifying procedures that they have performed, identifying drugs they have administered, identifying other healthcare workers who were present at the same time. Traditionally these reporting activities have been time consuming and take away time the healthcare worker may otherwise have been able to spend in providing care to patients. The wearer of the smart visor 100 may command the smart visor application 116 to build a report 144 that is stored in the non-transitory portion of the memory 114. This report 144 can be progressively built throughout the encounter of the healthcare worker with the patient. The initial verification of patient identity can be documented by the smart visor application 116 in the report 144. The current vitals of the patient may be captured and stored in the report 144. Operations involving healthcare equipment may be captured and stored in the report 144, for example readouts and indications of the equipment may be stored. All of this can be taking place in the background transparently to the healthcare worker who is now freed to focus more on the patient. In some contexts, this report may be referred to as a report of actions taken by a healthcare worker during a visit with a patient.

When the healthcare worker has completed his or her encounter with the patient, the report 144 can be uploaded by the smart visor application 116 via the radio transceiver 126 via the cell site 128 and the network 130 to a data store 146 (or via an access point to the network 130 to the data store 146). Alternatively, the reports 144 may be stored in the non-transitory portion of the memory 114 during the work shift of the healthcare worker and downloaded via a secure link in an "action room" for healthcare workers where smart visors 100 are donned at the start of work shifts and doffed at the end of work shifts. The secure link may be provided by a short-range wireless link such as BlueTooth or WiFi or by a wired link to a report harvesting station/computer. In an embodiment, the action room may be provided with electromagnetic shielding, whereby to suppress emission of BlueTooth or WiFi signals from inside the action room to outside the action room, whereby to enhance security of downloading reports 144 from smart visors 100.

In an embodiment, the smart visor application 116 requests information on medical procedures and on drug interactions from a medical procedures server application 152 that executes on a computer 150. In an embodiment, the computer 150 is located in a private domain of a healthcare facility behind a firewall of a private network maintained by the healthcare facility. For example, the smart visor application 116 sends a request for information on a procedure via the radio transceiver 126, via the cell site 128, via the network 130 to the medical procedures server application 152. Alternatively, the radio transceiver 126 may send the request for information to an access point via the network 130 to the medical procedures server application 152. The information returned may be the detailed steps of performing a specific medical procedure. The information returned may be information about a specific drug—for example recommended dosages, possible adverse effects of the specific drug, interactions of the specific drug with other drugs. The information on the medical procedure and/or the information on the specific drug may be presented by the HUD projector 106 on the inside surface of the optical visor 104.

In an embodiment, the smart visor application 116 may request information from a hospital data server application 158 that executes on a computer 156. In an embodiment, the computer 156 is located in a private domain of a healthcare facility behind a firewall of a private network maintained by the healthcare facility. The hospital data may be stored in a data store 160 and may comprise information about what hospital rooms are in service and which are available for a new patient. The hospital data may comprise information that identifies what medical personnel are on duty and what their specialties are. The hospital data may comprise work schedules of medical personnel. The hospital data may comprise contact information for medical personnel.

In an embodiment, a plurality of sensors 162 associated with a patient may wirelessly communicate directly with the smart visor 100, for example via WiFi wireless link, via a BlueTooth wireless link (e.g., "BlueTooth pairing"), or via a cellular wireless link. The sensors 162 may be topically adhered to a patient or implanted in the patient. The sensors 162 may provide values of vital signs to the smart visor 100, for example heart rate, O2 saturation level, body temperature, blood sugar level, blood thickness, blood pressure, or other vital sign. In an embodiment, the sensors 162 may provide values of patient body metrics to the smart visor 100. These patient body metrics may include what are traditionally considered vital signs but may further include other measured physical characteristics of a patient not normally deemed vital signs. Some of the sensors 162 may capture an electrocardiogram of the patient. In an embodiment, one item of healthcare equipment or a plurality of healthcare equipment 164 may wireless communicate directly with the smart visor 100, for example via WiFi wireless link, via a BlueTooth wireless link (e.g., "BlueTooth pairing"), or via a cellular wireless link.

The smart visor 100 may present the vital signs and/or body metrics provided by the sensors 162 via the HUD projector 106 on the inside surface of the optical visor 104, for example when the wearer requests the vital signs to be presented. The smart visor 100 may transmit data comprising the values of the vital signs via the radio transceiver 126, via the cell site 128, via the network 130, to a data store, for example to data store 154 or to data store 160. Alternatively, the radio transceiver 126 may transmit the data via an access point via the network 130 to the data store 154. The smart visor 100 may present readouts or other indications received from the healthcare equipment 164 via the HUD projector 106 on the inside surface of the optical visor 104, for example when the wearer requests the vital signs to be presented. In an embodiment, the smart visor application 116 may determine where the wearer is looking, and when the wearer is looking at the healthcare equipment 164, the smart visor application 116 commands the HUD projector 106 to present the readout or other indication from the item of healthcare equipment 164 that the wearer is looking at on the inside surface of the optical visor 104.

In an embodiment, the digital camera 108 may capture a digital image of a part of the patient and provide the digital image to the smart visor application 116. The smart visor application 116 may process the received digital image, magnify a portion of the digital image, and cause the HUD projector 106 to present the magnified portion of the digital image on the inside surface of the optical visor 104.

In an embodiment, the smart visor 100 and/or the smart visor headband 102 may comprise a scanner for reading a patient wristband, a radio frequency identity (RFID) chip on a patient, or other tag on a patient, whereby to identify or corroborate identity of the patient. The scanner may read identity tags such as bar codes, 2-D bar codes, schott codes, Semacodes associated with equipment, monitors, tools, or medicines available for use with a patient. The scanner may assist the healthcare worker in checking and cross-checking procedures and identities. For example, a tagged vial with X drug and Y dosage may be scanned, confirmed against prescription, and then injected into a patient at a specific injection site where the injection site could be recommended and targeted by the smart healthcare visor 100 and/or the system 100. This injection site might be recommended by the smart healthcare visor 100 based on past sites and history. This process can be recorded, for example by capturing images (e.g., images of the drug, images of the site of the injection for this dose) by the camera 108.

Figure 3A:
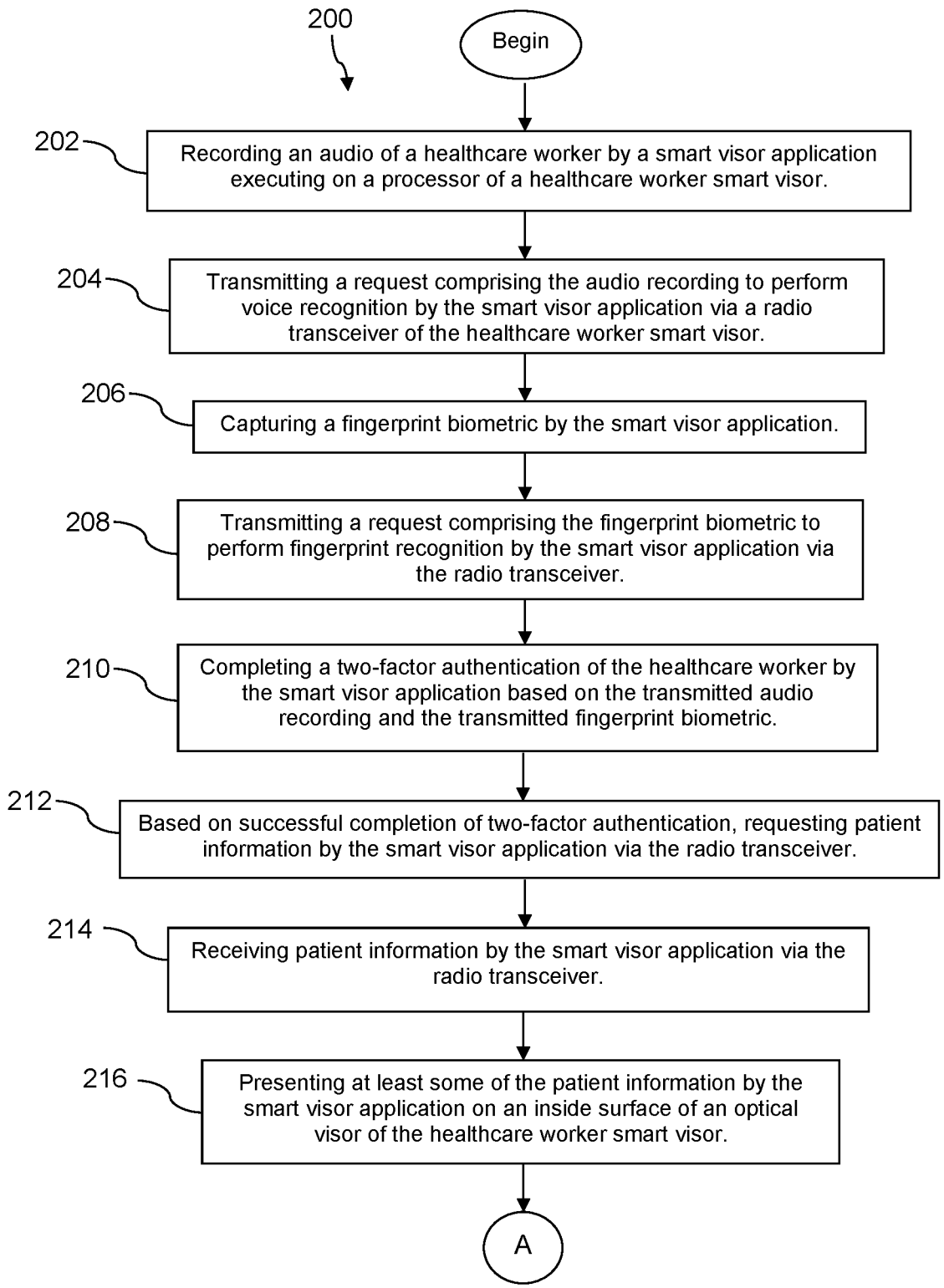
FIG. 3A and FIG. 3B are a flow chart of a method according to an embodiment of the disclosure.
Figure 3B:
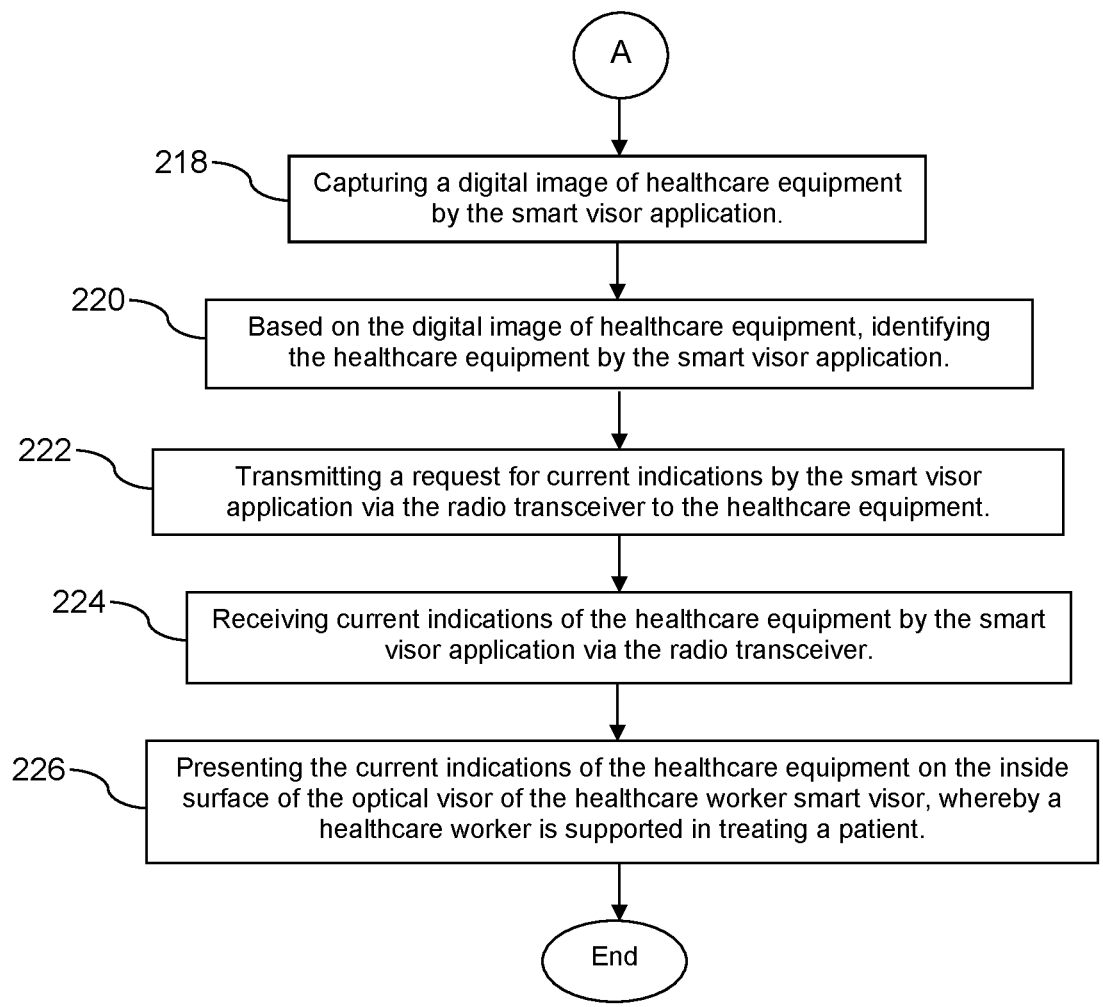

Turning now to FIG. 3A and FIG. 3B, a method 200 is described. In an embodiment, method 200 is a method of supporting a healthcare worker treat a patient. At block 202, the method 200 comprises recording an audio of a healthcare worker by a smart visor application executing on a processor of a healthcare worker smart visor. At block 204, the method 200 comprises transmitting a request comprising the audio recording to perform voice recognition by the smart visor application via a cellular radio transceiver of the healthcare worker smart visor. The request may be transmitted as a message containing the audio recording to a two-factor authentication server application, for example the two-factor authentication server application 134. The request may be transmitted as a plurality of messages, for example if the audio recording is larger than a single unsegmented message.

At block 206, the method 200 comprises capturing a fingerprint biometric by the smart visor application. At block 208, the method 200 comprises transmitting a request comprising the fingerprint biometric to perform fingerprint recognition by the smart visor application via the cellular radio transceiver. The request may be transmitted as a message containing the fingerprint biometric (e.g., a digital file) to the two-factor authentication server application. The request may be transmitted as a plurality of messages. In embodiment, the processing of block 202 and block 206 is performed and a single message or set of messages containing both the audio recording and the fingerprint biometric is sent together.

At block 210, the method 200 comprises completing a two-factor authentication of the healthcare worker by the smart visor application based on the transmitted audio recording and the transmitted fingerprint biometric. For example, the two-factor authentication server application 134 determines if the submitted audio recording and the fingerprint biometric match to the same person. The identity of the healthcare worker as claimed by the user of the smart visor 100 may be provided in the request(s) for two-factor authentication, and this provided identity may be used to search an entry in the data store 136 comprising an authoritative audio recording and an authoritative fingerprint biometric against which to compare the audio recording and fingerprint biometric transmitted by the smart visor 100.

At block 212, the method 200 comprises, based on successful completion of two-factor authentication, requesting patient information by the smart visor application via the cellular radio transceiver. In an embodiment, the method 200 comprises scanning an identity bracelet of a patient by the healthcare worker smart visor and analyzing a scan of the identity bracelet of the patient by the smart visor application to determine an identity of the patient, wherein requesting patient information by the smart visor application in block 212 comprises sending a patient information request message comprising the identity of the patient via the cellular radio transceiver. Alternatively, in a different embodiment, the method 200 comprises identifying a patient by capturing a digital image of a face of the patient by a digital camera of the healthcare worker smart visor and completing a facial recognition procedure by the smart visor application with a facial recognition server application that executes on a computer system, wherein requesting patient information by the smart visor application in block 212 comprises sending a patient information request message comprising the identity of the patient via the cellular radio transceiver.

At block 214, the method 200 comprises receiving patient information by the smart visor application via the cellular radio transceiver. At block 216, the method 200 comprises presenting at least some of the patient information by the smart visor application on an inside surface of an optical visor of the healthcare worker smart visor. In an embodiment, the method 200 further comprises receiving a voice command request to present patient information by the smart visor application, wherein presenting the at least some of the patient information by the smart visor application in block 216 is based on receipt of the voice command requesting presentation. In an embodiment, the method 200 further comprises receiving a voice command request to stop presentation of the patient information by the smart visor application and discontinuing presentation of the patient information by the smart visor application.

At block 218, the method 200 comprises capturing a digital image of healthcare equipment by the smart visor application. Alternatively, the processing at block 218 comprises scanning an identity indicator on the healthcare equipment, for example a bar code, a 2-D bar code, a schott code, a Semacode, RFID tag, or other identity indicator, and this identity information is captured. At block 220, the method 200 comprises based on the digital image of healthcare equipment, identifying the healthcare equipment by the smart visor application. This may comprise sending the digital image to a server application that looks up the identity of the healthcare equipment. This may comprise sending the identity information to the server application that looks up the identity of the healthcare equipment. In an embodiment, the smart visor application 116 may look up the identity of the equipment in the non-transitory portion of the memory 114 of the smart visor headband 102. Along with determining the identity of the healthcare equipment, the processing of block 220 may comprise obtaining a communication address and/or communication password that enables the smart visor application 116 to initiate a communication session with the healthcare equipment. At block 222, the method 200 comprises transmitting a request for current indications by the smart visor application via the cellular radio transceiver to the healthcare equipment. The processing of block 222 may comprise using the identity and/or the communication address of the healthcare equipment determined in the processing of block 220.

At block 224, the method 200 comprises receiving current indications of the healthcare equipment by the smart visor application via the cellular radio transceiver. At block 226, the method 200 comprises presenting the current indications of the healthcare equipment on the inside surface of the optical visor of the healthcare worker smart visor, whereby a healthcare worker is supported in treating a patient. In an embodiment, the method 200 further comprises receiving indications of vital signs of the patient by the smart visor application from sensors associated with the patient and presenting indications of the vital signs of the patient by the smart visor application on the inside surface of the optical visor. In an embodiment, the method 200 further comprises capturing information about a patient visit by the smart visor application, adding the captured information about the patient visit by the smart visor application to a patient visit record, and uploading the captured information by the smart visor application via the cellular radio transceiver to a data store.

Figure 4A:
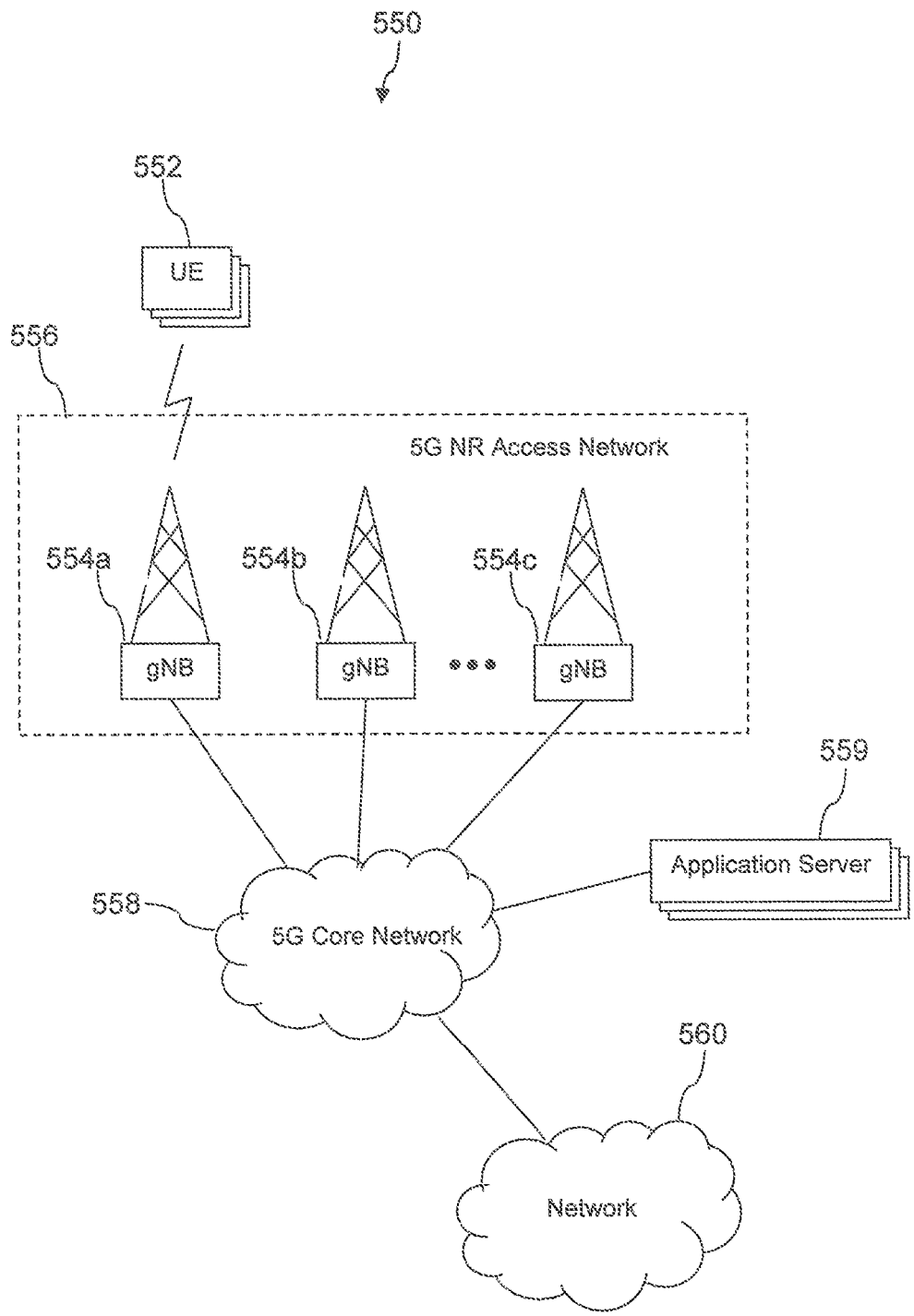
FIG. 4A and FIG. 4B are block diagrams of a 5G communication network according to an embodiment of the disclosure.

Turning now to FIG. 4A, an exemplary communication system 550 is described. In an embodiment, at least part of the network 130 described above with reference to FIG. 2A and FIG. 2B is provided by the communication system 550. In an embodiment, the healthcare worker smart visor 100 described above with reference to FIG. 1A, FIG. 1B, FIG. 2A, FIG. 2B, FIG. 3A, and FIG. 3B may be considered to be a user equipment (UE) such as UE 552. In an embodiment, some of the sensors 162 and/or some of the equipment 164 described above with reference to FIG. 2B may be considered to be UEs 552 from the point of view as being wireless communication devices or comprising a wireless communication device embedded in them. Typically, the communication system 550 includes a number of access nodes 554 that are configured to provide coverage in which UEs 552 such as cell phones, tablet computers, machine-type-communication devices, tracking devices, embedded wireless modules, and/or other wirelessly equipped communication devices (whether or not user operated), can operate. The access nodes 554 may be said to establish an access network 556. The access network 556 may be referred to as a radio access network (RAN) in some contexts. In a 5G technology generation an access node 554 may be referred to as a gigabit Node B (gNB). In 4G technology (e.g., long term evolution (LTE) technology) an access node 554 may be referred to as an evolved Node B (eNB). In 3G technology (e.g., code division multiple access (CDMA) and global system for mobile communication (GSM)) an access node 554 may be referred to as a base transceiver station (BTS) combined with a base station controller (BSC). In some contexts, the access node 554 may be referred to as a cell site or a cell tower. In some implementations, a picocell may provide some of the functionality of an access node 554, albeit with a constrained coverage area. Each of these different embodiments of an access node 554 may be considered to provide roughly similar functions in the different technology generations.

In an embodiment, the access network 556 comprises a first access node 554a, a second access node 554b, and a third access node 554c. It is understood that the access network 556 may include any number of access nodes 554. Further, each access node 554 could be coupled with a core network 558 that provides connectivity with various application servers 559 and/or a network 560. In an embodiment, at least some of the application servers 559 may be located close to the network edge (e.g., geographically close to the UE 552 and the end user) to deliver so-called "edge computing." The network 560 may be one or more private networks, one or more public networks, or a combination thereof. The network 560 may comprise the public switched telephone network (PSTN). The network 560 may comprise the Internet. With this arrangement, a UE 552 within coverage of the access network 556 could engage in air-interface communication with an access node 554 and could thereby communicate via the access node 554 with various application servers and other entities.

The communication system 550 could operate in accordance with a particular radio access technology (RAT), with communications from an access node 554 to UEs 552 defining a downlink or forward link and communications from the UEs 552 to the access node 554 defining an uplink or reverse link. Over the years, the industry has developed various generations of RATs, in a continuous effort to increase available data rate and quality of service for end users. These generations have ranged from "1G," which used simple analog frequency modulation to facilitate basic voice-call service, to "4G"— such as Long Term Evolution (LTE), which now facilitates mobile broadband service using technologies such as orthogonal frequency division multiplexing (OFDM) and multiple input multiple output (MIMO).

Recently, the industry has been exploring developments in "5G" and particularly "5G NR" (5G New Radio), which may use a scalable OFDM air interface, advanced channel coding, massive MIMO, beamforming, mobile mmWave (e.g., frequency bands above 24 GHz), and/or other features, to support higher data rates and countless applications, such as mission-critical services, enhanced mobile broadband, and massive Internet of Things (IoT). 5G is hoped to provide virtually unlimited bandwidth on demand, for example providing access on demand to as much as 20 gigabits per second (Gbps) downlink data throughput and as much as 10 Gbps uplink data throughput. Due to the increased bandwidth associated with 5G, it is expected that the new networks will serve, in addition to conventional cell phones, general internet service providers for laptops and desktop computers, competing with existing ISPs such as cable internet, and also will make possible new applications in internet of things (IoT) and machine to machine areas.

In accordance with the RAT, each access node 554 could provide service on one or more radio-frequency (RF) carriers, each of which could be frequency division duplex (FDD), with separate frequency channels for downlink and uplink communication, or time division duplex (TDD), with a single frequency channel multiplexed over time between downlink and uplink use. Each such frequency channel could be defined as a specific range of frequency (e.g., in radio-frequency (RF) spectrum) having a bandwidth and a center frequency and thus extending from a low-end frequency to a high-end frequency. Further, on the downlink and uplink channels, the coverage of each access node 554 could define an air interface configured in a specific manner to define physical resources for carrying information wirelessly between the access node 554 and UEs 552.

Without limitation, for instance, the air interface could be divided over time into frames, subframes, and symbol time segments, and over frequency into subcarriers that could be modulated to carry data. The example air interface could thus define an array of time-frequency resource elements each being at a respective symbol time segment and subcarrier, and the subcarrier of each resource element could be modulated to carry data. Further, in each subframe or other transmission time interval (TTI), the resource elements on the downlink and uplink could be grouped to define physical resource blocks (PRBs) that the access node could allocate as needed to carry data between the access node and served UEs 552.

In addition, certain resource elements on the example air interface could be reserved for special purposes. For instance, on the downlink, certain resource elements could be reserved to carry synchronization signals that UEs 552 could detect as an indication of the presence of coverage and to establish frame timing, other resource elements could be reserved to carry a reference signal that UEs 552 could measure in order to determine coverage strength, and still other resource elements could be reserved to carry other control signaling such as PRB-scheduling directives and acknowledgement messaging from the access node 554 to served UEs 552. And on the uplink, certain resource elements could be reserved to carry random access signaling from UEs 552 to the access node 554, and other resource elements could be reserved to carry other control signaling such as PRB-scheduling requests and acknowledgement signaling from UEs 552 to the access node 554.

The access node 554, in some instances, may be split functionally into a radio unit (RU), a distributed unit (DU), and a central unit (CU) where each of the RU, DU, and CU have distinctive roles to play in the access network 556. The RU provides radio functions. The DU provides L1 and L2 real-time scheduling functions; and the CU provides higher L2 and L3 non-real time scheduling. This split supports flexibility in deploying the DU and CU. The CU may be hosted in a regional cloud data center. The DU may be co-located with the RU, or the DU may be hosted in an edge cloud data center.

In an embodiment, an edge computing node or a local breakout feature may be used to handle some communication traffic to avoid this traffic being handled deep inside the 5G core network 558. Scenarios could be (1) a hospital covered by a private 5G network, which has a local mini-core network; (2) a wireless carrier provides an iUPF (inserted User Plane Functional node) for local breakout and supports a traffic path: from cell gNB to iUPF to Application Server; (3) a fully functional edge computing node that runs computation locally (including application server 559 plus communications UPF). This kind of edge processing may reduce latency and save long haul transport, thereby both improving communication quality of service and decreasing the burden on the network (e.g., the burden deep inside the 5G core network 558). In an embodiment, some gNBs 554 may connect to an edge node in the 5G core network 558 and then the application server 559. In an embodiment, the application server may connect to the 5G core network 558 tangentially—via an edge node or edge router to connect the application server 559 to the network 560 to access native cloud/Internet services. In an embodiment, the smart visor application 116, the two-factor authentication server application 134, the facial recognition server application 140, the medical procedures server application 152, the hospital data server application 158, and/or other applications executing in the system 101 described above with reference to FIG. 2A and FIG. 2B may leverage the 5G multiple network slices for supporting service level agreements and security assurance. Up to 8 network slices can be supported in 5G per 3GPP release 15 & 16. In an embodiment, each of the different applications of system 101 may be assigned a different network slice. This network slicing architecture of system 101 may be supported by the network slice selection function 574 described below with reference to FIG. 4B.

Figure 4B:
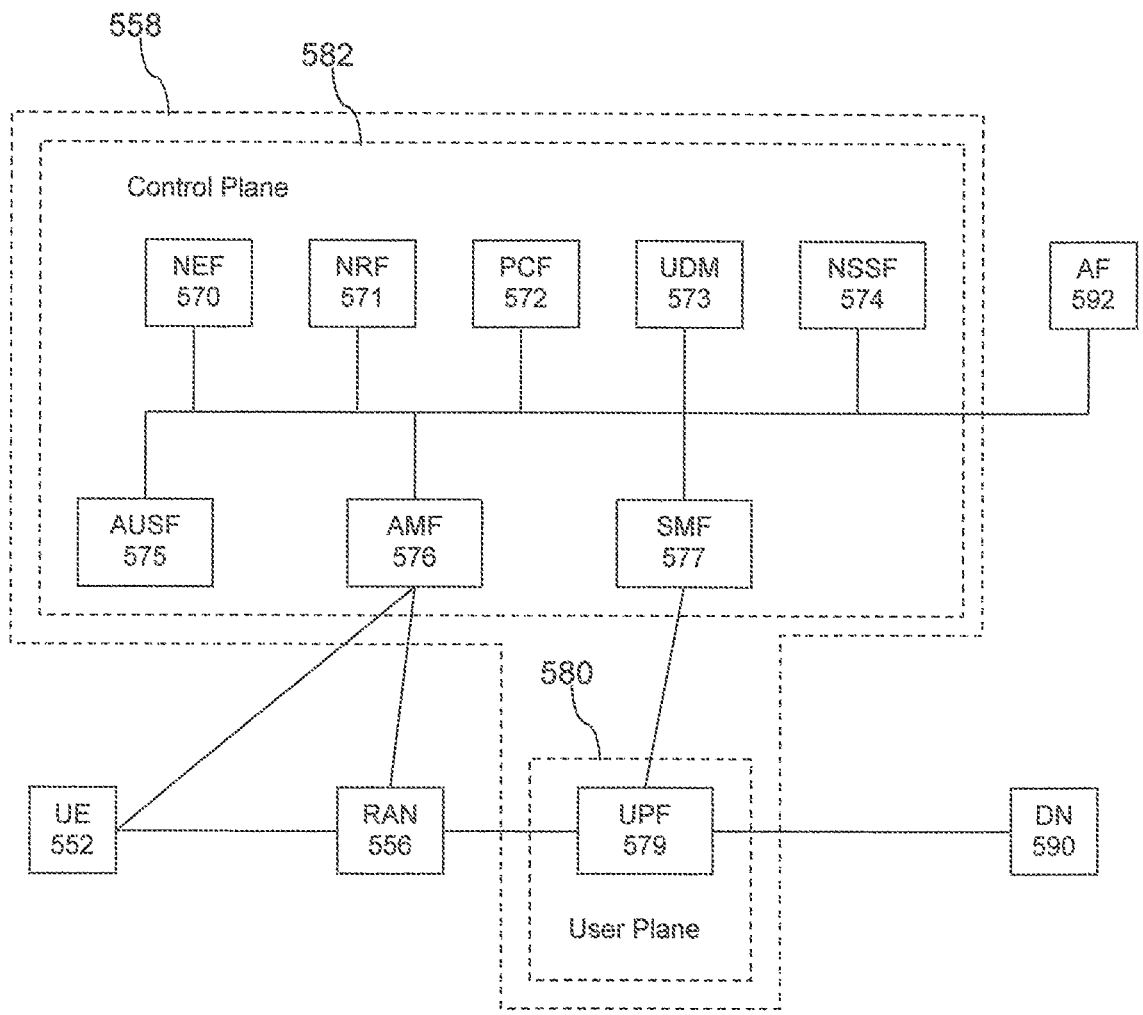

Turning now to FIG. 4B, further details of the core network 558 are described. In an embodiment, the core network 558 is a 5G core network. 5G core network technology is based on a service based architecture paradigm. Rather than constructing the 5G core network as a series of special purpose communication nodes (e.g., an HSS node, a MME node, etc.) running on dedicated server computers, the 5G core network is provided as a set of services or network functions. These services or network functions can be executed on virtual servers in a cloud computing environment which supports dynamic scaling and avoidance of long-term capital expenditures (fees for use may substitute for capital expenditures). These network functions can include, for example, a user plane function (UPF) 579, an authentication server function (AUSF) 575, an access and mobility management function (AMF) 576, a session management function (SMF) 577, a network exposure function (NEF) 570, a network repository function (NRF) 571, a policy control function (PCF) 572, a unified data management (UDM) 573, a network slice selection function (NSSF) 574, and other network functions. The network functions may be referred to as virtual network functions (VNFs) in some contexts.

Network functions may be formed by a combination of small pieces of software called microservices. Some microservices can be re-used in composing different network functions, thereby leveraging the utility of such microservices. Network functions may offer services to other network functions by extending application programming interfaces (APIs) to those other network functions that call their services via the APIs. The 5G core network 558 may be segregated into a user plane 580 and a control plane 582, thereby promoting independent scalability, evolution, and flexible deployment.

The UPF 579 delivers packet processing and links the UE 552, via the access network 556, to a data network 590 (e.g., the network 560 illustrated in FIG. 4A). The AMF 576 handles registration and connection management of non-access stratum (NAS) signaling with the UE 552. Said in other words, the AMF 576 manages UE registration and mobility issues. The AMF 576 manages reachability of the UEs 552 as well as various security issues. The SMF 577 handles session management issues. Specifically, the SMF 577 creates, updates, and removes (destroys) protocol data unit (PDU) sessions and manages the session context within the UPF 579. The SMF 577 decouples other control plane functions from user plane functions by performing dynamic host configuration protocol (DHCP) functions and IP address management functions. The AUSF 575 facilitates security processes.

The NEF 570 securely exposes the services and capabilities provided by network functions. The NRF 571 supports service registration by network functions and discovery of network functions by other network functions. The PCF 572 supports policy control decisions and flow based charging control. The UDM 573 manages network user data and can be paired with a user data repository (UDR) that stores user data such as customer profile information, customer authentication number, and encryption keys for the information. An application function 592, which may be located outside of the core network 558, exposes the application layer for interacting with the core network 558. In an embodiment, the application function 592 may be execute on an application server 559 located geographically proximate to the UE 552 in an "edge computing" deployment mode. The core network 558 can provide a network slice to a subscriber, for example an enterprise customer, that is composed of a plurality of 5G network functions that are configured to provide customized communication service for that subscriber, for example to provide communication service in accordance with communication policies defined by the customer. The NSSF 574 can help the AMF 576 to select the network slice instance (NSI) for use with the UE 552.

Figure 5:
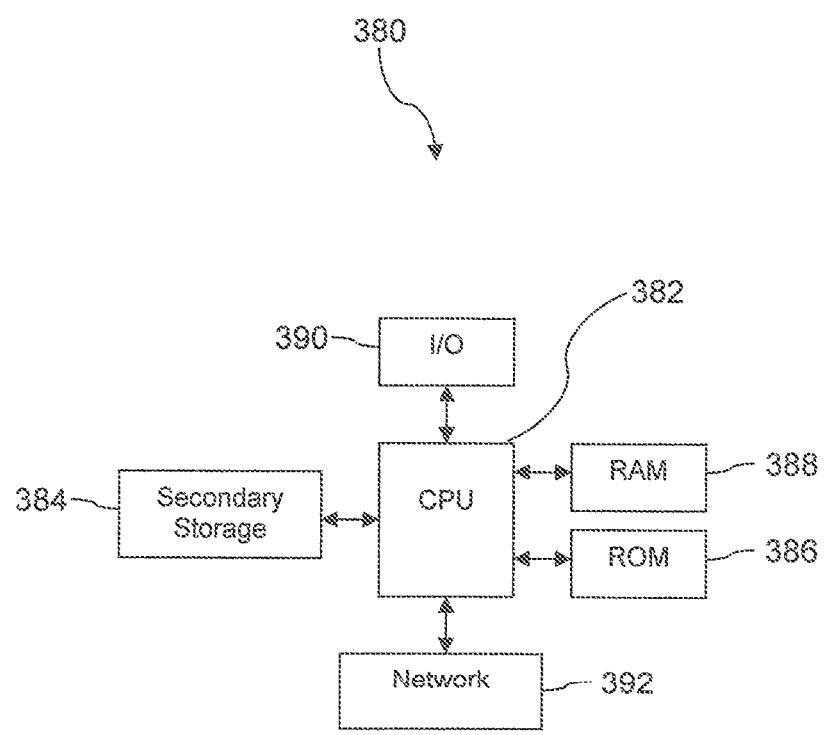
FIG. 5 is a block diagram of a computer system according to an embodiment of the disclosure.

FIG. 5 illustrates a computer system 380 suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards, and/or other well-known network devices. The network connectivity devices 392 may provide wired communication links and/or wireless communication links (e.g., a first network connectivity device 392 may provide a wired communication link and a second network connectivity device 392 may provide a wireless communication link). Wired communication links may be provided in accordance with Ethernet (IEEE 802.3), Internet protocol (IP), time division multiplex (TDM), data over cable service interface specification (DOCSIS), wavelength division multiplexing (WDM), and/or the like. In an embodiment, the radio transceiver cards may provide wireless communication links using protocols such as code division multiple access (CDMA), global system for mobile communications (GSM), long-term evolution (LTE), WiFi (IEEE 802.11), Bluetooth, Zigbee, narrowband Internet of things (NB IoT), near field communications (NFC), and radio frequency identity (RFID). The radio transceiver cards may promote radio communications using 5G, 5G New Radio, or 5G LTE radio communication protocols. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embodied in the carrier wave, or other types of signals currently used or hereafter developed, may be generated according to several methods well-known to one skilled in the art. The baseband signal and/or signal embodied in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third-party provider. Some cloud computing environments may comprise cloud computing resources owned and operated by the enterprise as well as cloud computing resources hired and/or leased from a third-party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A healthcare worker smart visor, comprising:
   a radio transceiver;
   a non-transitory memory;
   a camera;
   a processor communicatively coupled to the radio transceiver, the non-transitory memory, and the camera;
   an optical visor;
   a head-up display (HUD) projector that is communicatively coupled to the processor and that is operable to project an image on an inside surface of the optical visor;
   a headband retaining the radio transceiver, the non-transitory memory, the camera, the processor, the optical visor, and the HUD projector; and
   a smart visor application stored in the non-transitory memory that, when executed by the processor:
   transmits a digital image captured by the camera via the radio transceiver to a facial recognition server application that executes on a computer system,
   receives an identity of a patient via the radio transceiver in response to transmitting the digital image captured by the camera,
   transmits a request for patient information via the radio transceiver to a patient information server application executing on a computer system, wherein the request comprises the identity of the patient associated with the digital image,
   receives patient information via the radio transceiver in response to transmitting the request for patient information,
   presents at least some of the patient information on the inside surface of the optical visor via the HUD projector,
   receives patient body metrics via the radio transceiver from sensors associated with the patient,
   presents at least some of the body metrics on the inside surface of the optical visor, whereby a healthcare worker positively identifies the patient and provides healthcare to the patient according to an authorized treatment regime,
   receives a voice prompt from the healthcare worker wearing the healthcare worker smart visor requesting information on interactions with a specific drug, and
   presents information about interactions with the specific drug on the inside surface of the optical visor via the head-up display projector,
   wherein the HUD projector is configured to:
   receive information from the camera about an environment in front of the healthcare worker smart visor; and
   adapt the presentation of the at least some of the patient information to not obstruct a view of an object in the environment in front of the healthcare worker smart visor with the at least some of the patient information.

2. The healthcare worker smart visor of claim 1, wherein the smart visor application further creates a report of actions taken by a healthcare worker during a visit with a patient and stores the report.

3. The healthcare worker smart visor of claim 1, wherein the smart visor application processes a digital image received from the camera, magnifies a portion of the digital image, and causes the HUD projector to present the magnified portion of the digital image on the inside surface of the optical visor.

4. The healthcare worker smart visor of claim 1, wherein the radio transceiver is a cellular radio transceiver and further comprising a second radio transceiver configured to provide a WiFi wireless communication link or a BlueTooth wireless communication link.

5. The healthcare worker smart visor of claim 1, wherein the patient information comprises contact information, a treatment plan for the patient, a treatment history of the patient, a list of drugs taken by the patient, or a vital signs history of the patient.

6. The healthcare worker smart visor of claim 1, wherein the patient body metrics comprise heart rate, O2 saturation level, body temperature, blood sugar level, blood thickness, or blood pressure.

7. The healthcare worker smart visor of claim 1, wherein the radio transceiver is able to establish a wireless communication link according to a 5G, a long-term evolution (LTE), a code division multiple access (CDMA), or a global system for mobile communications (GSM) telecommunication protocol.

8. A healthcare worker smart visor, comprising:
   a radio transceiver;
   a non-transitory memory;
   a camera;

a processor communicatively coupled to the radio transceiver, the non-transitory memory, and the camera;
an optical visor;
a head-up (HUD) display projector that is communicatively coupled to the processor and that is operable to project an image on an inside surface of the optical visor, the projection having a focus point beyond the inside surface of the optical visor;
a headband retaining the radio transceiver, the non-transitory memory, the camera, the processor, the optical visor, and the head-up display projector; and
a smart visor application stored in the non-transitory memory that, when executed by the processor:
 performs two-factor authentication of a healthcare worker,
 transmits a digital image captured by the camera via the radio transceiver to a healthcare equipment recognition server application that executes on a computer system,
 receives an identity of the healthcare equipment via the radio transceiver in response to transmitting the digital image captured by the camera,
 transmits a request for current indications via the radio transceiver to the healthcare equipment based on the identity of the healthcare equipment,
 presents the current indications on the inside surface of the optical visor via the head-up display projector,
 receives patient information via the radio transceiver in response to transmitting a request for patient information,
 presents at least some of the patient information on the inside surface of the optical visor via the head-up display projector,
 receives a voice prompt from a healthcare worker wearing the healthcare worker smart visor requesting information on interactions with a specific drug,
 presents information about interactions with the specific drug on the inside surface of the optical visor via the head-up display projector;
wherein the HUD projector is configured to:
 receive information from the camera about an environment in front of the healthcare worker smart visor; and
 adapt the presentation of the at least some of the patient information to not obstruct a view of an object in the environment in front of the healthcare worker smart visor with the at least some of the patient information.

9. The healthcare worker smart visor of claim 8, wherein the smart visor application does not transmit via the radio transceiver, does not receive via the radio transceiver, and does not present on the via the head-up display projector until after successfully performing the two-factor authentication.

10. The healthcare worker smart visor of claim 8, wherein the presentations on the inside surface of the optical visor are focused at a mid-range.

11. The healthcare worker smart visor of claim 8, wherein the radio transceiver is a WiFi radio transceiver or a BlueTooth radio transceiver.

12. The healthcare worker smart visor of claim 8, wherein the optical visor is configured to attenuate communication of pathogens between a patient and a wearer of the healthcare worker smart visor and between the wearer and the patient.

13. The healthcare worker smart visor of claim 8, wherein the radio transceiver is able to establish a wireless communication link according to a 5G, a long-term evolution (LTE), a code division multiple access (CDMA), or a global system for mobile communications (GSM) telecommunication protocol.

* * * * *